(12) United States Patent
Hanada et al.

(10) Patent No.: US 7,964,179 B2
(45) Date of Patent: Jun. 21, 2011

(54) COSMETIC HAIR PREPARATION

(75) Inventors: Yoko Hanada, Wakayama (JP); Nakako Sato, Wakayama (JP)

(73) Assignee: Kao Corporation, Tokyo (JP)

( * ) Notice: Subject to any disclaimer, the term of this patent is extended or adjusted under 35 U.S.C. 154(b) by 1136 days.

(21) Appl. No.: 10/517,375

(22) PCT Filed: Jun. 13, 2002

(86) PCT No.: PCT/JP02/05920
§ 371 (c)(1),
(2), (4) Date: Jun. 9, 2005

(87) PCT Pub. No.: WO03/105792
PCT Pub. Date: Dec. 24, 2003

(65) Prior Publication Data
US 2005/0255074 A1    Nov. 17, 2005

(51) Int. Cl.
*A61Q 5/02* (2006.01)
*A61Q 5/12* (2006.01)
*D06M 15/643* (2006.01)

(52) U.S. Cl. ............... 424/70.122; 106/287.11

(58) Field of Classification Search .......... 424/70; A61K 7/075
See application file for complete search history.

(56) References Cited

U.S. PATENT DOCUMENTS

| | | | | |
|---|---|---|---|---|
| 5,077,041 A | * | 12/1991 | Yamashina et al. | 510/121 |
| 5,078,990 A | * | 1/1992 | Martin et al. | 510/124 |
| 5,747,016 A | * | 5/1998 | Yui et al. | 424/401 |
| 6,086,663 A | * | 7/2000 | Kondo et al. | 106/287.11 |

FOREIGN PATENT DOCUMENTS

| | | |
|---|---|---|
| EP | 0 078 597 | 5/1983 |
| JP | 4-230615 | 8/1992 |
| JP | 5-70327 | 3/1993 |
| JP | 5-238920 | 9/1993 |
| JP | 8-208439 | 8/1996 |
| JP | 9-151119 | 6/1997 |
| JP | 1997-151119 | * 6/1997 |
| JP | 9-183854 | 7/1997 |
| JP | 9-194335 | 7/1997 |
| JP | 2000-128740 | 5/2000 |
| JP | 2000-143458 | 5/2000 |
| JP | 2001-513534 | 9/2001 |
| JP | 2002-179535 | 6/2002 |
| WO | 92 06899 | 4/1992 |
| WO | 93 10748 | 6/1993 |
| WO | 94 16677 | 8/1994 |
| WO | 99 09939 | 3/1999 |

OTHER PUBLICATIONS

JP 1997-151119 (manual translation—pdf).*
Koushouhin Kagaku, pp. 130-131.
Koushouhin Kagaku, pp. 308-311.

* cited by examiner

*Primary Examiner* — Robert A Wax
*Assistant Examiner* — Jeffrey T Palenik
(74) *Attorney, Agent, or Firm* — Oblon, Spivak, McClelland, Maier & Neustadt, L.L.P.

(57) ABSTRACT

The invention provides hair cosmetics which can suppress a frictional feeling of hair in running water during rinsing to improve softness and smoothness thereby preventing the hair from being damaged by twisting during rinsing, and comprises organopolysiloxane having an amino-modified organopolysiloxane chain and a polyoxyalkylene chain, and at least one cationic surfactant selected from compounds represented by formula (1) or (2):

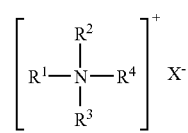

(1)

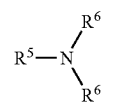

(2)

wherein at least one of $R^1$, $R^2$, $R^3$ and $R^4$ represents e.g. an alkyl group containing 8 to 35 carbon atoms in total, and the remainder represents a C1 to C5 alkyl group, hydroxyalkyl group etc., $X^-$ represents a halogen ion or an organic anion, $R^5$ represents e.g. an alkyl group containing 8 to 35 carbon atoms in total, and $R^6$ represents a C1 to C22 alkyl group etc.

24 Claims, No Drawings

COSMETIC HAIR PREPARATION

FIELD OF THE INVENTION

The present invention relates to hair cosmetics which is useful in suppressing a frictional feeling of hair during rinsing in running water and improving the softness and smoothness of hair during rinsing.

BACKGROUND OF THE INVENTION

The required performance of hair cosmetics is varied depending on each stage during washing, during rinsing, during wetting and after drying. There is strong demand particularly for improvement of softness and smoothness during rinsing and suppression of friction.

Conventionally, cationic compounds such as cationic surfactants and cationic polymers, lubricants, silicones etc. have been used to improve smoothness during rinsing, but the effect of the cationic surfactants and cationic polymers on suppression of a feeling of friction in water is limited, and is poor in an ability to confer softness and smoothness. The lubricants hardly suppress a feeling of friction in running water, and dimethyl polysiloxane can be said to be absent in an ability to suppress a feeling of friction in running water and in an ability to confer softness and smoothness. Among the silicones, a polyether-modified silicone is poor in an ability to confer a feeling of softness, and the ability thereof to suppress a feeling of friction and to confer smoothness is not durable. An amino-modified silicone can confer a lasting feeling of softness, but cancels the feeling of selfness because of its feeling of friction similar to the feeling of strong rubber in running water.

SUMMARY OF THE INVENTION

The present invention provides hair cosmetics which can suppress a frictional feeling of hair in running water during rinsing to improve softness and smoothness, whereby the damage to hair by twisting during rinsing can be prevented.

The present invention relates to hair cosmetics containing the following components (A) and (B):

(A) organopolysiloxane having an amino-modified organopolysiloxane chain and a polyoxyalkylene chain, (B) at least one cationic surfactant selected from compounds represented by formula (1) or (2):

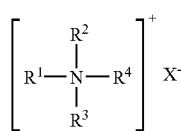

wherein at least one of $R^1$, $R^2$, $R^3$ and $R^4$ represents a linear or branched alkyl, alkenyl, or aliphatic acyloxy(polyethoxy)ethyl group containing 8 to 35 carbon atoms in total, which may be interrupted by a functional group represented by —O—, —CONH—, —OCO— or —COO— or substituted with —OH, and the remainder represents a $C_1$ to $C_5$ alkyl or hydroxyalkyl group, or a polyoxyethylene group wherein the number of moles added is 10 or less in total, and $X^-$ represents a halogen ion or an organic anion.

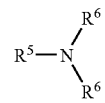

wherein $R^5$ represents a linear or branched alkyl or alkenyl group containing 8 to 35 carbon atoms in total, which may be interrupted by a functional group represented by —O—, —CONH—, —OCO— or —COO— or substituted with —OH, $R^6$ represents a $C_1$ to $C_{22}$ alkyl group, alkenyl group or hydroxyalkyl group, and two $R^6$s may be the same or different from each other.

DETAILED DESCRIPTION OF THE INVENTION

[Component (A)]

The amino-modified organopolysiloxane chain in component (A) used in the present invention is preferably the one having a polymerization unit represented by formula (3):

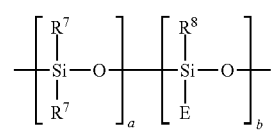

wherein $R^7$ represents a hydrogen atom or a $C_1$ to $C_6$ monovalent hydrocarbon group, $R^8$ represents $R^7$ or E wherein E represents a reactive functional group represented by —$R^9$—Z whereupon $R^9$ represents a direct bond or a $C_1$ to $C_{20}$ divalent hydrocarbon group, and Z represents a primary to tertiary amino group-containing group or an ammonium group-containing group, a is a number of 2 or more, b is a number of 1 or more, and a plurality of $R^7$, $R^8$ and E may be the same or different from one another.

In formula (3), $R^7$s are independent of one another, each of which is preferably a hydrogen atom, a $C_1$ to $C_6$ alkyl group or a phenyl group, more preferably a methyl group or an ethyl group, more preferably a methyl group.

$R^9$ is preferably a $C_1$ to $C_6$ linear or branched alkylene group such as a methylene group, ethylene group, trimethylene group, propylene group and tetramethylene group, more preferably a trimethylene group or propylene group.

a and b each represent the number of polymerizable repeating units, a is preferably a number of 2 to 1000, and b is preferably a number of 1 to 50.

Z is preferably an amino group-containing group or an ammonium group-containing group represented by formula (8) or (9).

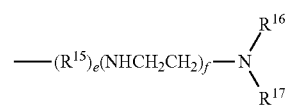

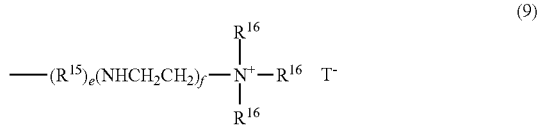

wherein $R^{15}$ represents $-OCH_2CH_2-$,

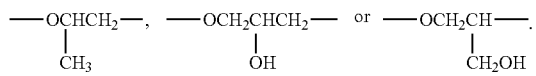

$R^{16}$ and $R^{17}$ each represent a hydrogen atom or a monovalent hydrocarbon group, and $R^{16}$s and $R^{17}$s may the same or different from each other, e and f each represent an integer of 0 to 6, and $T^-$ represents a halogen ion or an organic anion.

The group E is preferably $-(CH_2)_3-NH_2$, $-(CH_2)_3-N(CH_3)_2$, $-(CH_2)_3-NH-(CH_2)_2-NH_2$, $-(CH_2)_3-NH-(CH_2)_2-N(CH_3)_2$ or $-(CH_2)_3-N^+(CH_3)_3Cl^-$, more preferably $-(CH_2)_3-NH-(CH_2)_2-NH_2$. Examples of $T^-$ include halogen ions such as chlorine, iodine and bromine, and organic anions such as methosulfate, ethosulfate, methophosphate and ethophosphate. The average molecular weight of the amino-modified organopolysiloxane chain is preferably 250 to 10000.

The polyoxyalkylene chains in the component (A) may be the same or different, and each represent a polymer chain consisting of preferably $C_1$ to $C_5$ alkylene repeating units, more preferably ethylene and/or propylene repeating units. These may have any structures such as block polymer and random polymer, preferably block polymer. The average molecular weight of the polyoxyalkylene chain is preferably 200 to 10000.

The component (A) is preferably a block copolymer consisting of an amino-modified organopolysiloxane chain and a polyoxyalkylene chain, more preferably a block copolymer having a polymerization unit represented by formula (4) (referred to hereinafter as block copolymer (4)):

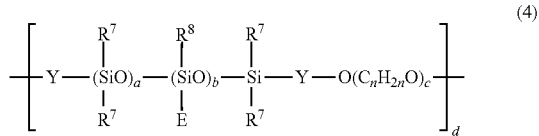

wherein $R^7$, $R^8$, E, a and b have the same meaning as defined above, n is a number of 2 to 10, and $n_s$ whose number is c may be the same or different from one another, c is a number of 4 or more, d is a number of 2 or more, and Y represents a divalent organic group bound via a carbon-silicon atom to the adjacent silicon atom and via an oxygen atom to the polyoxyalkylene block chain.

The divalent organic group represented by Y in formula (4) is preferably an alkylene group or an arylene group, more preferably a $C_1$ to $C_{12}$ alkylene group or a $C_6$ to $C_{12}$ arylene group, still more preferably an ethylene group, propylene group, trimethylene group, n-butylene group or i-butylene group, most preferably an n-butylene group or i-butylene group. Preferably, a is a number of 2 to 1000 and b is a number of 1 to 50. c is preferably a number of 4 to 200, and d is preferably a number of 2 to 100.

The ratio of the siloxane block in the block copolymer (4) is preferably 25 to 97 wt. %, more preferably 35 to 90 wt. %, still more preferably 50 to 80 wt. %, and the block copolymer (4) preferably has an average molecular weight of at least 1200.

The siloxane block refers to siloxane having two $R^7$ groups represented by $-[Si(R^7)_2-O]_a-$ and $-Si(R^7)_2-O-$, and the ratio of the siloxane block refers to the ratio (wt. %) of the molecular weight of the siloxane block to the molecular weight of the block copolymer (4).

This range is preferable because the block copolymer (4) is excellent in solubility or dispersibility in cosmetics and in retention in hair.

The average molecular weight in the present invention is a value determined in a usual manner by GPC using chloroform as eluent and polystyrene as standard.

Further preferable examples include amino-modified polysiloxane/polyoxyalkylene block copolymers having a polymerization unit represented by formula (10) (referred to hereinafter as block copolymer (10)):

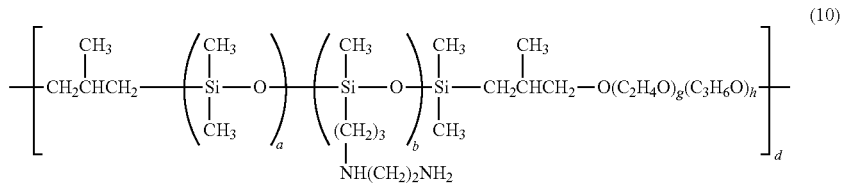

wherein a, b and d have the same meaning as defined above, g is an integer of 4 or more, and h is a number of 0 to 30.

In formula (10), it is preferable that a is a number of 2 to 1000, b is a number of 1 to 50, g is a number of 4 to 200, and d is a number of 2 to 100. By way of example, FZ-3789 from Nippon Unicar Co., Ltd. can be mentioned.

In the block copolymer (10), the ratio of the siloxane block is preferably 25 to 97 wt. %, more preferably 35 to 90 wt. %, still morepreferably 50 to 80 wt. %, relative to the whole of the copolymer, and the block copolymer (10) preferably has an average molecular weight of at least 1200.

The siloxane block refers to siloxane having dimethyl groups represented by $-[Si(CH_3)_2-O]_a-$ and $-Si(CH_3)_2-O-$ respectively, and the ratio of the siloxane block refers to the ratio (wt. %) of the molecular weight of the siloxane block to the molecular weight of the block copolymer (10).

This range is preferable because the block copolymer (10) is excellent in solubility or dispersibility in cosmetics and in retention in hair.

The kinematic viscosity of the component (A) containing the block copolymer (4) and the block copolymer (10) used in the present invention preferably has a viscosity of at least 10 $mm^2/s$, more preferably at least 100 $mm^2/s$, still more preferably at least 1,000 $mm^2/s$, even more preferably 5,000 mm$^2$/s. The kinematic viscosity is preferably not more than 1,000,000 mm$^2$/s, more preferably not more than 100,000 mm$^2$/s. This range is preferable because the component (A) is excellent in solubility or dispersibility in cosmetics and in retention in hair.

The viscosity was measured under the condition of 25° C. with rotor No. 2 at 6 rounds per minute (rpm) in a Brookfield viscometer.

The amine equivalent of the component (A) containing the block copolymer (4) and the block copolymer (10) used in the present invention is preferably at least 300 g/mol, more preferably at least 600 g/mol. The amine equivalent is preferably not more than 10,000 g/mol, more preferably not more than 5,000 g/mol, still more preferably not more than 2,500 g/mol. This range is preferable because the component (A) is excellent in solubility or dispersibility in cosmetics, reduces a frictional feeling upon rinsing and improves softness.

The amine equivalent (g/mol) can be determined by titration of an ethanol solution of the polymer with hydrochloric acid of known concentration.

These components (A) can be used alone or as a mixture of two or more thereof. The content of the component (A) in the hair cosmetics of the present invention is preferably 0.01 to 50 wt. %, more preferably 0.1 to 20 wt. %, still more preferably 0.1 to 10 wt. %, most preferably 0.1 to 5 wt. %, from the viewpoint of suppression of a frictional feeling of hair, improvement of the softness and smoothness of hair upon rinsing, and achievement of an excellent feeling in use.

The component (A) used in the present invention can be produced by a method described in, for example, JP-A 9-183854.

[Component (B)]

In the compound represented by formula (1), it is preferable that one, two or three of $R^1$, $R^2$, $R^3$ and $R^4$ represent a linear or branched alkyl, alkenyl, or aliphatic acyloxy(polyethoxy) ethyl group containing 8 to 35 carbon atoms in total (more preferably 8 to 26) (referred to hereinafter as long-chain group), which may be interrupted by a functional group represented by —O—, —CONH—, —OCO— or —COO— or substituted with —OH, and the remainder represents a C1 to C5 alkyl or hydroxyalkyl group, or a polyoxyethylene group wherein the number of moles added is 10 or less in total. Examples of the compound wherein one of $R^1$, $R^2$, $R^3$ and $R^4$ is the long-chain group include, for example, stearyl trimethyl ammonium chloride, hydroxy stearyl trimethyl ammonium chloride, capryl trimethyl ammonium chloride, myristyl trimethyl ammonium chloride, cetyl trimethyl ammonium chloride, cetyl triethyl ammonium bromide, behenyl trimethyl ammonium chloride, lauryl trimethyl ammonium chloride, N-stearyl-N,N,N-tri(polyoxyethylene) ammonium chloride (having 3 moles added therein) etc. Examples of the compound wherein two of $R^1$, $R^2$, $R^3$ and $R^4$ are each the long-chain group include, for example, distearyl dimethyl ammonium chloride, hardened tallow dialkyl dimethyl ammonium chloride, tallow dialkyl dimethyl ammonium bromide, dioleyl dimethyl ammonium chloride, dipalmityl methyl hydroxyethyl ammonium methosulfate, distearyl dimethyl ammonium chloride, diisostearyl dimethyl ammonium methosulfate, di[(2-dodecanoylamino)ethyl] dimethyl ammonium chloride and di[(2-stearoylamino)propyl] dimethyl ammonium ethosulfate etc. Examples of the compound wherein three of $R^1$, $R^2$, $R^3$ and $R^4$ are each the long-chain group include, for example, dioleyl monostearyl methyl ammonium chloride, dioleyl monobehenyl methyl ammonium chloride, trioleyl methyl ammonium chloride, tristearyl methyl ammonium methosulfate etc.

Other examples include branched quaternary ammonium salts represented by formula (11) or (12) and quaternary ammonium salts represented by formula (13).

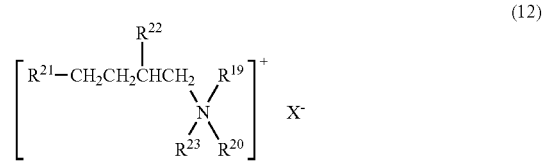

wherein $R^{18}$ is a mixture of (a) a branched alkyl group represented by $CH_3$—$(CH_2)_i$—$CH(R^{24})$—$CH_2$— wherein $R^{24}$ represents a methyl group or ethyl group, and i is such an integer that the total number of carbons in the alkyl group becomes 8 to 16 and (b) a linear alkyl group represented by $CH_3$—$(CH_2)_j$— wherein j is an integer of 7 to 15, wherein the degree [(a)/(a)+(b)] of the branched chain is 10 to 100 mol %. $R^{19}$ and $R^{20}$ each represent a C1 to C3 alkyl or hydroxyalkyl group. $R^{21}$ and $R^{22}$ each represent a C2 to C12 alkyl group. $R^{23}$ represents a group represented by $R^{21}$—$CH_2CH_2CH(R^{22})CH_2$— or a C1 to C3 alkyl group. $X^-$ has the same meaning as defined above.

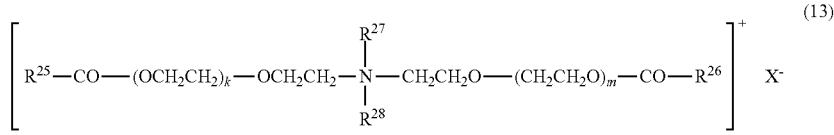

wherein $R^{25}$ and $R^{26}$ each represent a C8 to C22 alkyl or alkenyl group which may be substituted with a hydroxyl group. $R^{27}$ and $R^{28}$ each represent a C1 to C3 alkyl group or —$(CH_2CH_2O)_p$H wherein p is a number of 1 to 6. k and m each represent a number of 0 to 5. $X^-$ has the same meaning as defined above.

Examples of $X^-$ which is a counterion of the quaternary ammonium salt include halogen ions such as chlorine, iodine and bromine, and organic anions such as methosulfate, ethosulfate, methophosphate and ethophosphate.

Among these, the branched quaternary ammonium salt represented by formula (11) is synthesized usually from a starting material such as C8 to C16 oxoalcohol, and examples thereof include dialkyl dimethyl ammonium salts, dialkyl methyl hydroxyethyl ammonium salts etc., each of which has an alkyl group derived from oxoalcohol. In the present invention, those of formula (11) wherein the degree of the branched chain of $R^{18}$ is usually 10 to 100 mol %, particularly preferably 10 to 50 mol %, are preferably used. Those wherein the total number of atoms in $R^{18}$ is 8 to 16 are used, among which those having a uniform distribution are preferable, and particularly those having a distribution of 5 or less mol % $C_8$ to $C_{11}$, 10 to 35 mol % $C_{12}$, 15 to 40 mol % $C_{13}$, 20 to 45 mol % $C_{14}$, 5 to 30 mol % $C_{15}$, and 5 or less mol % $C_{16}$ are preferable.

Examples of such branched quaternary ammonium salt include dialkyl dimethyl ammonium chloride having a C8 to C16 alkyl group wherein the degree of the branched chain is 10 to 50 mol %.

The branched quaternary ammonium salt represented by formula (12) is synthesized usually from $C_8$ to $C_{28}$ Guerbet alcohol ($R^{21}$—$CH_2CH_2C(-R^{22})$—$HCH_2OH$) as a starting material. Preferable examples of the branched quaternary ammonium salt include, for example, alkyl trimethyl ammonium salts, dialkyl dimethyl ammonium salts, dialkyl methyl hydroxy ethyl ammonium salts etc., each of which has an alkyl group derived from $C_8$ to $C_{28}$ Guerbet alcohol. Particularly preferable among these compounds are 2-decyl tetradecyl trimethyl ammonium chloride, 2-dodecyl hexadecyl trimethyl ammonium chloride, di-2-hexyl decyl dimethyl ammonium chloride, di-2-octyl dodecyl dimethyl ammonium chloride etc.

The quaternary ammonium salts represented by formula (13) include those described in, for example, WO93/10748, WO92/06899, WO94/16677 etc. Particularly preferable among these salts are those of formula (13) wherein each of $R^{25}$ and $R^{26}$ is an oleyl group or a $C_{12}$ to 18 alkyl group, $R^{27}$ is a methyl group, $R^{28}$ is —$CH_2CH_2OH$, and each of k and m is 0.

Preferable examples of the quaternary salt having an alkyl or alkenyl group interrupted by a functional group represented by —OCO— or —COO— include quaternary ammonium salts represented by formula (14) or (15) described in JP-A 2000-128740 or JP-A 2000-143458.

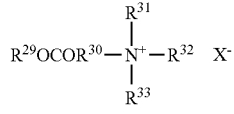

(14)

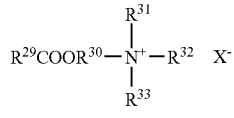

(15)

wherein $R^{29}$ represents a $C_7$ to $C_{37}$ alkyl or alkenyl group; $R^{30}$ represents a $C_1$ to $C_5$ alkylene group; $R^{31}$, $R^{32}$ and $R^{33}$ each represent a $C_1$ to $C_4$ alkyl or hydroxyalkyl group; and $X^-$ has the same meaning as defined above.

In formulae (14) and (15), $R^{29}$ is preferably a $C_7$ to $C_{21}$, particularly $C_{11}$ to $C_{18}$, linear or branched alkyl or alkenyl group. $R^{30}$ is preferably an ethylene group or n-propylene group. Each of $R^{31}$, $R^{32}$ and $R^{33}$ is preferably a methyl group, ethyl group, hydroxyethyl group or hydroxypropyl group. Specific examples of $X^-$ include a halogen ion such as $Cl^-$ and $Br^-$, a $C_1$ to $C_5$ alkyl sulfate ion ($CH_3SO_4^-$, $C_2H_5SO_4^-$, $C_3H_7SO_4^-$ etc.), an alkyl carbonate ion ($CH_3CO_2^-$) etc., among which $Cl^-$, $Br^-$, $CH_3SO_4^-$, $C_2H_5SO_4^-$ and $CH_3CO_3^-$ are preferable.

Further preferable among the quaternary ammonium salts represented by formula (1) are long-chain monoalkyl quaternary ammonium salts wherein $R^1$ is a $C_{12}$ to $C_{22}$ linear alkyl or alkenyl group, and each of $R^2$, $R^3$ and $R^4$ is a $C_1$ to $C_3$ alkyl group, as well as those dialkyl quaternary ammonium salts having $C_8$ to $C_{16}$ alkyl groups wherein the degree of branched chain is 10 to 50 mol %, represented by formula (11), particularly long-chain monoalkyl quaternary ammonium salts wherein $R^1$ is a $C_{12}$ to $C_{22}$ linear alkyl or alkenyl group, and each of $R^2$, $R^3$ and $R^4$ is a $C_1$ to $C_3$ alkyl group.

In the tertiary amine represented by formula (2), $R^5$ is preferably a linear or branched alkyl or alkenyl group containing 8 to 26 carbon atoms in total, which may be interrupted by a functional group represented by —O—, —CONH—, —OCO— or —COO— or substituted with —OH, $R^6$ is preferably a $C_1$ to $C_5$ alkyl group, alkenyl group or hydroxyalkyl group, and two $R^6$s may be the same or different from each other. Specific examples of the tertiary amine represented by formula (2) include distearyl methylamine, dioleyl methylamine, dipalmitoyl methylamine, stearyl dimethylamine, stearyl diethylamine, behenyl dimethylamine, behenyl diethylamine, oleyl dimethylamine, palmitoyl dimethylamine etc.

Examples of the compound wherein $R^5$ is an alkyl or alkenyl group having 8 to 35 carbon atoms in total, which may be interrupted by —CONH—, include amide amines represented by formula (16):

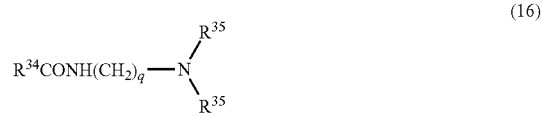

(16)

wherein $R^{34}$ is a $C_{16}$ to $C_{22}$ alkyl or alkenyl group, $R^{35}$s each represent a $C_1$ to $C_3$ alkyl group, and q is a number of 1 to 3.

Examples of the amide amines represented by formula (16) include stearamide propyl dimethylamine, stearamide propyl diethylamine, stearamide ethyl diethylamine, stearamide ethyl dimethylamine, palmitamide propyl dimethylamine, palmitamide propyl diethylamine, palmitamide ethyl diethylamine, palmitamide ethyl dimethylamine, behenamide propyl dimethylamine, behenamide propyl diethylamine, behenamide ethyl diethylamine, behenamide ethyl dimethylamine, arachidamide propyl dimethylamine, arachidamide propyl diethylamine, arachidamide ethyl diethylamine, arachidamide ethyl dimethylamine, and mixtures thereof, among which stearamide propyl dimethylamine, stearamide ethyl diethylamine and mixtures thereof are preferable.

When the tertiary amine and amide amine are used as salt, an organic acid and/or an inorganic acid is added depending on pH. The organic and inorganic acids include, for example, phosphoric acid, hydrochloric acid, acetic acid, L-glutamic acid, lactic acid, malic acid, succinic acid, fumaric acid, tartaric acid and mixtures thereof, among which L-glutamic acid, lactic acid, hydrochloric acid and mixtures thereof are preferable.

The tertiary amine represented by formula (2) is more preferably a long-chain monoalkyl tertiary amine wherein $R^5$ is a $C_{12}$ to 22 linear alkyl or alkenyl group, $R^6$s each represent a $C_1$ to $C_3$ alkyl group, or an amide amine represented by formula (16).

These components (B) may be used alone or as a mixture of two or more thereof, and the content of the component (B) in the hair cosmetics of the present invention is preferably 0.001 to 20 wt. %, more preferably 0.005 to 15 wt. %, still more preferably 0.1 to 10 wt. %, most preferably 0.1 to 5 wt. %, from the viewpoint of suppression of a frictional feeling of hair, improvement of the softness and smoothness of hair upon rinsing, and achievement of an excellent feeling in use.

[Lubricant]

The hair cosmetics of the present invention is blended preferably with a lubricant to improve a feeling of moistness without stickiness. Such lubricant is preferably at least one member selected from compounds represented by formulae (5), (6) and (7):

$$R^{10}-OH \quad (5)$$

$$R^{11}-COOH \quad (6)$$

$$\begin{array}{l} CH_2O-R^{12} \\ | \\ CHO-R^{13} \\ | \\ CH_2O-R^{14} \end{array} \quad (7)$$

wherein $R^{10}$ represents a $C_{12}$ to $C_{30}$ alkyl or alkenyl group; $R^{11}$ represents a $C_{11}$ to $C_{29}$ alkyl or alkenyl group; and at least one of $R^{12}$, $R^{13}$ and $R^{14}$ represents a $C_8$ to $C_{30}$ acyl group, and the remainder represents a hydrogen atom.

These compounds include, for example, $C_{12}$ to $C_{30}$ saturated or unsaturated alcohols; $C_{12}$ to $C_{30}$ saturated or unsaturated fatty acids; and mono-, di- or triglycerides having a $C_8$ to $C_{30}$ saturated or unsaturated fatty acid residue.

The $C_{12}$ to $C_{30}$ saturated or unsaturated alcohols include, for example, n-dodecyl alcohol, myristyl alcohol, cetyl alcohol, stearyl alcohol, oleyl alcohol, behenyl alcohol, ceryl alcohol, myricyl alcohol, caranaubile alcohol, arachin alcohol, octyldodecyl alcohol etc. Esters of these alcohols and $C_1$ to $C_{10}$ fatty acids, for example, cetyl 2-ethylhexanoate, diisostearyl malate etc. are also preferably added.

The $C_{12}$ to $C_{30}$ saturated or unsaturated fatty acid includes lauric acid, myristic acid, palmitic acid, stearic acid, isostearic acid, behenic acid, cerotic acid, coconut fat and oil fatty acid, oleic acid, 18-methyl eicosanoic acid etc. Esters of these fatty acids and $C_1$ to $C_{10}$ alcohols, for example, isopropyl myristate, isopropyl palmitate etc. are also preferably added.

The mono-, di- or triglycerides having a $C_8$ to $C_{30}$ saturated or unsaturated fatty acid residue include palmitic acid monoglyceride, behenic acid monoglyceride, myristic acid monoglyceride, isostearic acid monoglyceride, isostearic acid diglyceride, decanoic acid monoglyceride, lauric acid monoglyceride, stearic acid monoglyceride, oleic acid monoglyceride, myristic acid diglyceride, 1-palmitoyl/oleic acid glyceride, stearic acid triglyceride etc.

Among the compounds represented by formulae (5), (6) and (7) above, those represented by formula (5) are preferable because they feel less oily and are not influenced by water hardness.

At least one kind of these lubricants can be used, and is blended preferably in an amount of 0.01 to 30 wt. %, more preferably 0.05 to 20 wt. %, still more preferably 0.1 to 10 wt. % in the hair cosmetics of the present invention, to achieve a sufficient effect and an excellent feeling in use.

[Other Components]

Further, silicones are added preferably to the hair cosmetics of the present invention to improve smoothness after drying, and act effectively with high adsorptivity by hydrophobic interaction with component (A).

The silicones include, for example, the following (i) to (xi):
(i) dimethyl polysiloxane represented by formula (17):

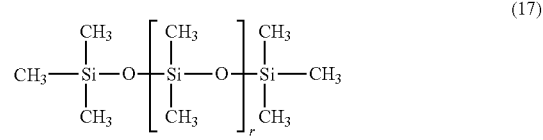

wherein r is a number of 3 to 20000.
(ii) methylphenyl polysiloxane,
(iii) amino-modified silicone, An amino-modified silicone having a polymerization unit represented by formula (3) but not having a polyoxyalkylene chain is preferable, for example SM8704C (manufactured by Toray Silicone) and DC939 (manufactured by Dow Corning),
(iv) fatty acid-modified polysiloxane,
(v) alcohol-modified silicone,
(vi) aliphatic alcohol-modified polysiloxane,
(vii) polyether-modified silicone,
(viii) epoxy-modified silicone,
(ix) fluorine-modified silicone,
(x) cyclic silicone, and
(xi) alkyl-modified silicone.

Among these silicones, the above-mentioned (i) [wherein in formula (17), r can be selected from a number of 3 to 20000, depending on purposes such as finish feeling, but is preferably 100 to 1000, for hair cosmetics of light-finish type], (iii), (vi), (vii) and (x) are preferable in the case of the hair cosmetics of the present invention, among which (i) is more preferable to improve smoothness after drying.

The content of the silicones in the hair cosmetics of the present invention is preferably 0.01 to 20 wt. %, more preferably 0.1 to 10 wt. %, from the viewpoint of exhibiting a feel unique to silicone and excellent stability of the products.

Further, incorporation of at least one member selected from α-hydroxy acid, β-hydroxy acid, 1,2-dicarboxylic acid, 1,3-dicarboxylic acid, aromatic carboxylic acid, amino acid, urea, guanidine, aromatic alcohol and/or a salt thereof into the hair cosmetics of the present invention is preferable because of improvement in hair setting. The salt includes alkali metal salts, alkaline earth metal salts, amine salts, ammonium salts, alkanol amine salts, basic amino acid salts, and salts of component (A) and/or component (B), and the presence of the component (A) and/or component (B) in the forms of salts in the hair cosmetics is effective.

Specific examples include malic acid, succinic acid, maleic acid, salicylic acid, malonic acid, mandelic acid, lactic acid, glycolic acid or salts thereof, glycine, urea, phenyl urea, citrulline, thiourea, guanidine, methyl salicylate, salicylic acid ethylene glycol, N-methyl-2-pyridone etc.

At least one of these compounds can be used, and is contained in an amount of preferably 0.1 to 50 wt. %, more preferably 0.5 to 30 wt. %, still more preferably 0.5 to 20 wt. %, in the hair cosmetics of the present invention.

[Hair Cosmetics]

The compounding ratio [(A)/(B)] of the compound (A) to the compound (B) in the hair cosmetics of the present invention is preferably in the range of 10/1 to 1/10 by weight, more preferably 3/1 to 1/3. From the viewpoint of emulsion stability, the ratio of the component (A) to the lubricant is preferably in the range of 10/1 to 1/10, more preferably 1/1 to 1/10.

The pH of the hair cosmetics of the present invention is preferably pH 2.5 to 8, more preferably 3 to 7, still more preferably 3 to 5.

Not only the components described above but also components used in usual hair cosmetics, such as oils such as hydrocarbon and silicone oil; humectants such as glycerin, propylene glycol, 1,3-butylene glycol and polyethylene glycol; surfactants such as anionic surfactant, nonionic surfactant and amphoteric surfactant; efficacious agents such as antidandruff agent and vitamins; preservatives such as paraben; feel improvers and thickeners such as water-soluble polymers, for example cationic cellulose, cationic guar gum and hydroxyethyl cellulose; coloring agents such as dyes and pigments; pearling agents such as glycol esters; and other chelating agents, various perfumes, etc. can be incorporated into the hair cosmetics of the present invention in such a range that the effect of the present invention is not deteriorated.

The hair cosmetics of the present invention can be produced in a usual manner, and are formed preferably into a hair rinse, hair conditioner, hair treatment, rinse-in-shampoo, hair foam and hair gel, more preferably into after-shampoos and pre-shampoos such as a hair rinse, hair conditioner and hair treatment. The pre-shampoos are conditioners used by being applied uniformly onto hair before shampooing and then rinsed lightly with water or not rinsed, followed by shampooing in a usual manner.

The hair treated with the hair cosmetics of the present invention is excellent in softness and smoothness in a state wetted with water, particularly in softness and smoothness in running water, and is not frictional upon rinsing. Further, the lift-up of cuticles can be prevented, so damage to hair can be prevented and repaired. In the whole process of from bubbling with a shampoo to the end of rinsing, the hair has a lasting feeling of softness and smoothness without any feeling of friction. The component (A) in the present invention, that is, the organopolysiloxane having an amino-modified organopolysiloxane chain and a polyoxyalkylene chain, is highly soluble or dispersible in cosmetics and can adhere relatively uniformly to the surface of hair. This solubility or dispersibility also depends on the structure of the component (A) and the pH of the hair cosmetics, and is particularly excellent at pH 2.5 to 8.

EXAMPLES

In the Examples, % is % by weight unless otherwise specified. The total amount of each composition in the Examples is 100% by weight.

Example 1 and Comparative Examples 1 to 4

The hair rinses of the present invention having the compositions shown in Table 1 using copolymers 1 to 5 represented by the following formulae and FZ-3789 (amino-modified organopolysiloxane/polyoxyalkylene block copolymer manufactured by Nippon Unicar Co., Ltd.) as component (A), and comparative rinses having the compositions shown in Table 2 without using component (A), were produced in a usual manner. Copolymer 1:

Copolymer 1:

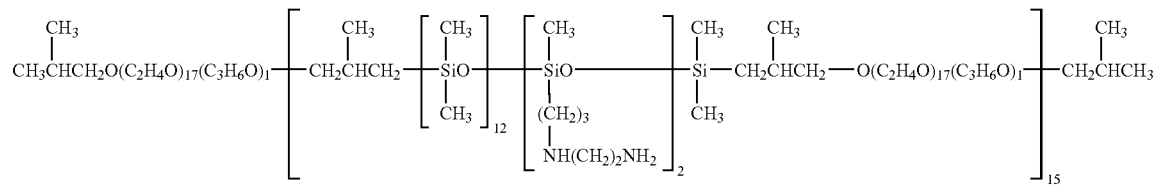

Copolymer 2:

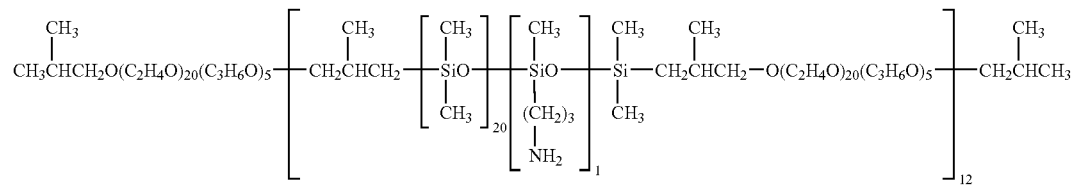

Copolymer 3:

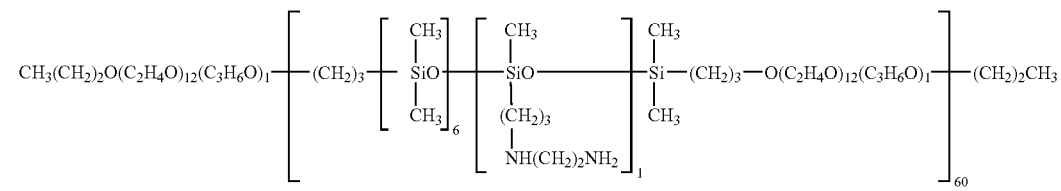

Copolymer 4:

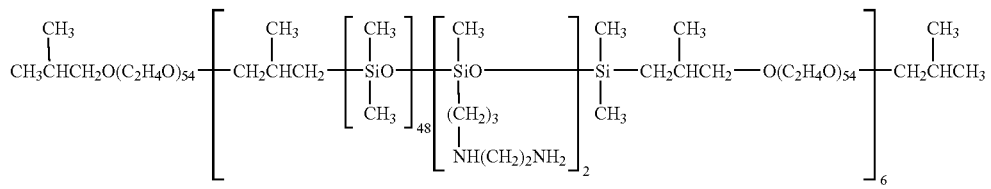

Copolymer 5:

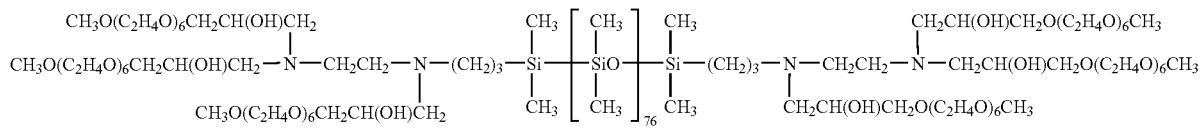

After shampooing with a standard shampoo shown below, the hair of a monitor was parted in the middle, and the hair rinse of the invention or the comparative hair rinse produced above was applied to one side of the hair, and a standard hair rinse shown below was applied to the other side, and a feeling of friction in running water during rinsing, softness and smoothness were evaluated according to the following standards. Thereafter, the hair was dried, and easiness in hair setting and smoothness were evaluated according to the following standards. Then, the hair was re-shampooed with a standard shampoo shown below, and a feeling of friction during rinsing, softness and smoothness were evaluated according to the following standards. The results are shown in Tables 1 and 2.

After treatment with the rinse of the invention and drying, 4 hairs were cut, dipped in a 10-fold aqueous dilution of the standard shampoo shown below, and observed with a digital microscope, and as a result, cuticle lift-up was not observed. On the other hand, the hair dried after treatment with the standard hair rinse shown below, cuticle lift-up was observed.

<Composition of standard shampoo>

| | |
|---|---|
| 25% polyoxyethylene lauryl ether sodium sulfate (Number of moles of ethylene oxide added on average = 2.5) | 62% |
| Lauric acid diethanol amide | 2.3% |
| Disodium edate | 0.1% |
| Sodium benzoate | 0.5% |
| Sodium chloride | 0.8% |
| 75% phosphoric acid | suitable amount |
| Perfume, methyl paraben | suitable amount |
| Purified water | balance |
| pH | 6.5 |

<Composition of standard hair rinse>

| | |
|---|---|
| Stearyl trimethyl ammonium chloride | 2% |
| Cetyl alcohol | 3% |
| Propylene glycol | 1% |
| Citric acid | suitable amount |
| Perfume | suitable amount |
| Methyl paraben | suitable amount |
| Purified water | balance |
| pH | 4.8 |

<Evaluation Standards>

Evaluated under the following standards by 10 monitors.
⊙: Evaluated by all monitors to be effective as compared with the standard hair rinse.
○: Evaluated by 7 to 9 monitors to be effective as compared with the standard hair rinse.
Δ: Evaluated by 4 to 6 monitors to be effective as compared with the standard hair rinse.
x: Evaluated by 3 or less monitors to be effective as compared with the standard hair rinse.

TABLE 1

| | | | Products of the invention | | | | | | | |
|---|---|---|---|---|---|---|---|---|---|---|
| | | | 1 | 2 | 3 | 4 | 5 | 6 | 7 | 8 |
| Hair rinse (%) | Component A | FZ-3789 | | | | | | | | 1 |
| | | Copolymer 1 | 1 | | | | 5 | 10 | | |
| | | Copolymer 2 | | 3 | | | | | | |
| | | Copolymer 3 | | | | 1.5 | | 1 | 10 | |
| | | Copolymer 4 | | | | 0.5 | | 1 | | |
| | | Copolymer 5 | | | | | 5 | | | |
| | Component B | Behenyl trimethyl ammmonium chloride | 3 | 1 | | | | | | |
| | | Stearyl trimethyl ammonium chloride | | 2 | 2 | | 2 | | | |
| | | Dicetyl dimethyl ammonium chloride | | | | | 1 | | | |
| | | Behenyl dimethyl amine | | | | 5 | | 3 | | 1 |
| | | Stearamide propyl dimethylamine | | | | | | | 3 | 2 |
| | Lubricant | Cetyl alcohol | | 4 | | | 1 | | | 1 |
| | | Stearyl alcohol | | | 1 | | 1 | | 1 | 3 |
| | | Behenyl alcohol | 3 | 2 | 7 | 1 | 9 | 2 | | |

TABLE 1-continued

| | | Products of the invention | | | | | | | |
|---|---|---|---|---|---|---|---|---|---|
| | | 1 | 2 | 3 | 4 | 5 | 6 | 7 | 8 |
| Other components | Cyclic silicone pentamer | 3.5 | 3 | | | 3.5 | 3 | | |
| | Dimethyl polysiloxane (TSF451-10A manufactured by GE Toshiba Silicones Co., Ltd.) | 0.7 | 0.7 | 1.4 | 0.4 | 0.4 | 0.4 | 0.4 | 0.7 |
| | Dimethyl polysiloxane (TSF451-50MA manufactured by GE Toshiba Silicones Co., Ltd.) | 0.3 | 0.3 | 0.6 | 0.2 | 0.2 | 0.2 | 0.2 | 0.3 |
| | Lactic acid | | | | | 3 | 3 | 3 | 2 |
| | Malic acid | | | 2 | 1 | 5 | 3 | | 3 |
| | Citric acid | Suitable amount | Suitable amount | Suitable amount | Suitable amount | Suitable amount | Suitable amount | Suitable amount | Suitable amount |
| | 2-Naphthalene sulfonic acid | | | 1 | 1 | 0.5 | | | |
| | Propylene glycol | 1 | 1 | 1 | 1 | 1.5 | 1.5 | 1 | 0.5 |
| | Perfume | Suitable amount | Suitable amount | Suitable amount | Suitable amount | Suitable amount | Suitable amount | Suitable amount | Suitable amount |
| | Methyl paraben | Suitable amount | Suitable amount | Suitable amount | Suitable amount | Suitable amount | Suitable amount | Suitable amount | Suitable amount |
| | Purified water | Balance | Balance | Balance | Balance | Balance | Balance | Balance | Balance |
| | pH | 4.8 | 4.8 | 4.8 | 4.8 | 4.8 | 4.8 | 4.8 | 4.8 |
| Result of the evaluation | Absence of frictional feeling during rinsing | ◎ | ○ | ◎ | ○ | ◎ | ◎ | ○ | ◎ |
| | Softness during rinsing | ◎ | ◎ | ○ | ◎ | ◎ | ◎ | ○ | ◎ |
| | Smoothness during rinsing | ◎ | ◎ | ○ | ◎ | ◎ | ◎ | ◎ | ◎ |
| | Easiness of hair setting after drying | ○ | ○ | ◎ | ◎ | ◎ | ◎ | ◎ | ◎ |
| | Smoothness of hair after drying | ◎ | ◎ | ◎ | ◎ | ◎ | ◎ | ◎ | ◎ |
| | Absence of frictional feeling during rinsing after re-shampooing | ◎ | ○ | ◎ | ○ | ◎ | ◎ | ○ | ◎ |
| | Softness during rinsing after re-shampooing | ◎ | ◎ | ○ | ◎ | ◎ | ◎ | ○ | ◎ |
| | Smoothness during rinsing after re-shampooing | ◎ | ◎ | ○ | ◎ | ◎ | ◎ | ◎ | ◎ |

TABLE 2

| | | | Comparative products | | | |
|---|---|---|---|---|---|---|
| | | | 1 | 2 | 3 | 4 |
| Hair rinse (%) | Component B | Behenyl trimethyl ammonium chloride | | 3 | | |
| | | Stearyl trimethyl ammoium chloride | 2 | | | 2 |
| | | Behenyl dimethyl amine | | | 3 | |
| | Lubricant | Cetyl alcohol | 1 | | | 3 |
| | | Stearyl alcohol | 2 | | | |
| | | Behenyl alcohol | | 3 | 6 | |
| | Other components | Dimethyl polysiloxane (TSF451-10A manufactured by GE Toshiba Silicones Co., Ltd.) | 3 | 2 | | |
| | | Amino-modidifed polysiloxane (KF-8002 manufactured by Shin-etsu silicone) | | 1 | | 5 |
| | | Polyether modified polysiloxane (TSF4452 manufactured by GE Toshiba Silicones Co., Ltd.) | | | 1 | |
| | | Lactic acid | | | 3 | |
| | | Citric acid | Suitable amount | Suitable amount | Suitable amount | Suitable amount |
| | | Propylene glycohl | 1 | 1 | 1 | 1 |
| | | Perfume | Suitable amount | Suitable amount | Suitable amount | Suitable amount |
| | | Methyl paraben | Suitable amount | Suitable amount | Suitable amount | Suitable amount |
| | | Purified water | balance | balance | balance | balance |
| | | pH | 4.8 | 4.8 | 4.8 | 4.8 |
| Result of the evaluation | | Absence of frictional feeling during rinsin | △ | X | △ | X |
| | | Softness during rinsing | △ | ○ | X | △ |
| | | Smoothness during rinsing | △ | △ | ○ | ○ |
| | | Easiness of hair setting after drying | △ | △ | ○ | △ |
| | | Smootheness of hair after drying | ○ | ○ | △ | ○ |
| | | Absence of frictional feeling during rinsing after re-shampooing | △ | X | △ | X |
| | | Softness during rinsing after re-shampooing | △ | △ | X | △ |
| | | Smoothness during rinsing after re-shampooing | △ | △ | △ | ○ |

Example 2

A conditioning shampoo having the following composition was produced in a usual manner.

| | |
|---|---|
| Polyoxyethylene lauryl ether sodium sulfate (Number of moles of ethylene oxide added on average = 2.5) | 10.0% |
| Stearyl dimethylamine | 0.1% |
| Cetyl dimethylamine | 0.1% |
| Acetal | 0.5% |
| Amino-modified polysiloxane/polyoxyalkylene block copolymer (FZ-3789 manufactured by Nippon Unicar) | 1.0% |
| Dimethyl polysiloxane (TSF451-10A manufactured by GE Toshiba Silicones) | 0.7% |
| Dimethyl polysiloxane (TSF451-50MA manufactured by GE Toshiba Silicones) | 0.3% |
| Lauryl dimethyl amine oxide | 1.0% |
| Lauryl carboxymethyl hydroxyethyl imidazolium betaine | 1.0% |
| Cationic cellulose | 0.5% |
| Propylene glycol | 0.5% |
| Ethylene glycol distearate | 2.0% |
| 50% aqueous citric acid | suitable amount |
| Perfume, methyl paraben | suitable amount |
| Purified water | balance |
| pH | 3.5 |

This conditioning shampoo had a strong feeling of softness and smoothness during bubbling, and had no feeling of friction during rinsing, to exhibit a feeling of softness and smoothness. After treatment and drying, 4 hairs were cut, dipped in a 10-fold aqueous dilution of the same standard shampoo (referred to hereinafter as pre-shampoo) as in Example 1, and observed with a digital microscope, and as a result, cuticle lift-up was not observed at all.

Example 3

A hair treatment having the following composition was prepared in a usual manner.

| | |
|---|---|
| Behenyl trimethyl ammonium chloride | 8.0% |
| Behenyl alcohol | 7.0% |
| Amino-modified polysiloxane/polyoxyalkylene block copolymer (FZ-3789 manufactured by Nippon Unicar) | 5.0% |
| Dimethyl polysiloxane (TSF451-10A manufactured by GE Toshiba Silicones) | 0.7% |
| Dimethyl polysiloxane (TSF451-50MA manufactured by GE Toshiba Silicones) | 0.3% |
| Monostearic acid polyoxyethylene sorbitan (Number of moles of ethylene oxide added on average = 20) | 0.5% |
| Behenic acid | 1.0% |
| Dipropylene propylene glycol | 6.0% |
| Glycerin | 10.0% |
| 50% aqueous citric acid | suitable amount |
| Perfume, methyl paraben | suitable amount |
| Purified water | balance |
| pH | 4.8 |

This hair treatment had a strong feeling of softness and smoothness upon application, and had no feeling of friction during rinsing, to exhibit a feeling of softness and smoothness. When the pre-shampoo was used, the feeling of softness and smoothness was maintained without friction from bubbling to rinsing. After treatment and drying, 4 hairs were cut, dipped in a 10-fold aqueous dilution of the pre-shampoo, and observed with a digital microscope, and as a result, cuticle lift-up was not observed at all.

Example 4

A conditioning hair foam having the following composition was prepared in a usual manner.

| | |
|---|---|
| <Stock solution> | |
| Stearyl trimethyl ammonium chloride | 0.5% |
| Cetyl trimethyl ammonium chloride | 0.5% |
| Salicylic acid | 0.3% |
| Cationic cellulose (Polymer JR-400 manufactured by UCC) | 0.5% |
| Monostearic acid polyoxyethylene sorbitan (15E.O.) | 0.5% |
| Amino-modified polysiloxane/polyoxyalkylene block copolymer (FZ-3789 manufactured by Nippon Unicar) | 5.0% |
| Dimethyl polysiloxane (TSF451-10A manufactured by GE Toshiba Silicones) | 0.7% |
| Dimethyl polysiloxane (TSF451-50MA manufactured by GE Toshiba Silicones) | 0.3% |
| Diglycerin | 5.0% |
| 50% aqueous citric acid | suitable amount |
| Cetyl 2-ethyl hexanoate | 2.0% |
| Rosemary extract | 0.1% |
| Ethanol | 15.0% |
| Vitamin E | 0.05% |
| Perfume | 0.1% |
| Purified water | balance |
| <Charging> | |
| Stock solution | 90% |
| LPG | 10% |
| pH | 6.5 |

When the pre-shampoo was used, this conditioning hair foam maintained a feeling of softness and smoothness after application and drying without friction from bubbling to rinsing.

After treatment and drying, 4 hairs were cut, dipped in a 10-fold aqueous dilution of the pre-shampoo, and observed with a digital microscope, and as a result, cuticle lift-up was not observed at all.

Example 5

A hair conditioning gel having the following composition was prepared in a usual manner.

| | |
|---|---|
| Cetyl trimethyl ammonium chloride | 5.0% |
| Sodium 2-naphthalene sulfonate | 2.0% |
| Salicylic acid | 0.3% |
| Glycerin | 5.0% |
| Oleic acid monoglyceride | 0.2% |
| Amino-modified polysiloxane/polyoxyalkylene block copolymer (FZ-3789 manufactured by Nippon Unicar) | 5.0% |
| Dimethyl polysiloxane (TSF451-10A manufactured by GE Toshiba Silicones) | 0.7% |
| Dimethyl polysiloxane (TSF451-50MA manufactured by GE Toshiba Silicones) | 0.3% |
| 50% aqueous citric acid | suitable amount |
| Perfume | 0.1% |
| Purified water | balance |
| pH | 6.5 |

When the pre-shampoo was used, this hair conditioning gel maintained a feeling of softness and smoothness after application and drying without friction from bubbling to rinsing.

After treatment and drying, 4 hairs were cut, dipped in a 10-fold aqueous dilution of the pre-shampoo, and observed with a digital microscope, and as a result, cuticle lift-up was not observed at all.

Example 6

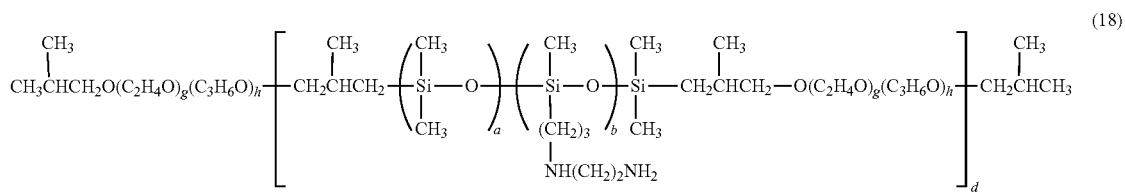

Using amino-modified polysiloxane/polyoxyethylene block copolymers 6 to 8 (hereinafter referred to simply as copolymers 6 to 8) represented by formula (18) above wherein a, b, d, g and h are values shown in Table 3, a hair rinse having the following composition was produced in a usual manner. As a comparative product, a hair rinse having the same composition as above except that block copolymers 6 to 8 were not contained was produced. A professional panel (one person) was shampooed with the same standard shampoo as in Example 1, and these hair rinses were applied to hair, and the absence of a feeling of friction during rinsing, and softness, were evaluated under the standards below. The results are shown in Table 3.

| <Hair rinse composition> | |
| --- | --- |
| Behenyl trimethyl ammonium chloride | 2.0% |
| Behenyl alcohol | 7.0% |
| Copolymers 6 to 8 | 5.0% |
| Dimethyl polysiloxane (TSF451-10A manufactured by GE Toshiba Silicones) | 0.7% |
| Dimethyl polysiloxane (TSF451-50MA manufactured by GE Toshiba Silicones) | 0.3% |

| <Hair rinse composition> | |
| --- | --- |
| Behenic acid | 1.0% |
| Dipropylene glycol | 6.0% |
| Malic acid | 5.0% |
| 50% aqueous citric acid | suitable amount |
| Perfume, methyl paraben | suitable amount |
| Purified water | balance |
| pH | 3.0 |

<Evaluation Standards>

⊙: During rinsing, the hair hardly feels frictional and feels soft.

○: During rinsing, the hair feels slightly frictional and feels slightly soft.

Δ: During rinsing, the hair feels frictional and does not feel so soft.

x: During rinsing, the hair feels strongly frictional and does not feel soft.

TABLE 3

| | | Block polymer of formula (18) | | | | | | Results of evaluation during rinsing | |
| --- | --- | --- | --- | --- | --- | --- | --- | --- | --- |
| | Component A | a | b | g | h | d | Ratio of siloxane block (wt. %) | Absence of feeling of friction | Softness |
| Product of the invention | Copolymer 6 | 11 | 1 | 17 | 0 | 24 | 46 | ⊙ | ○ |
| | Copolymer 7 | 20 | 2 | 17 | 0 | 24 | 56 | ⊙ | ⊙ |
| | Copolymer 8 | 40 | 4 | 17 | 0 | 50 | 67 | ⊙ | ⊙ |
| Comparative product | None | | | | | | — | Δ | X |

Example 7

A hair rinse (after-shampoo) having the following composition was produced in a usual manner.

| | |
|---|---|
| Dialkyl dimethyl ammonium chloride | 3.0% |
| (Coatamine D2345P manufactured by Kao) | |
| Polyoxyethylene lauryl ether (EO = 4) | 5.0% |
| (Emulgen 104P manufactured by Kao) | |
| Isostearyl glyceryl ether | 2.0% |
| (Penetol GE-IS manufactured by Kao) | |
| Dimethyl polysiloxane | 0.1% |
| (TSF451-50MA manufactured by GE Toshiba Silicones) | |
| Copolymer 8 | 0.2% |
| Citric acid | suitable amount |
| Perfume, methyl paraben | suitable amount |
| Water | balance |
| pH | 3.0 |

This hair rinse (after-shampoo) had a strong feeling of softness and smoothness upon application, without any feeling of friction during rinsing, to exhibit a feeling of softness and smoothness. When the same standard shampoo as in Example 1 was used after drying, the feeling of softness and smoothness were maintained without friction from bubbling to rinsing.

After treatment and drying, 4 hairs were cut, dipped in a 10-fold aqueous dilution of the same standard shampoo as in Example 1, and observed with a digital microscope, and as a result, cuticle lift-up was not observed at all.

Example 8

A pre-shampoo having the following composition was produced in a usual manner.

| | |
|---|---|
| Hydroxyethyl cellulose | 1% |
| (HEC Daicel SE-850K manufactured by Daicel Chemical Industries) | |
| Polyethylene glycol | 1% |
| (Polyox WSR-N60K manufactured by Dow Chemical Japan) | |
| Copolymer 8 | 1% |
| Lactic acid | suitable amount |
| Perfume, methyl paraben | suitable amount |
| Water | balance |
| pH | 3.0 |

This pre-shampoo was applied onto wetted hair and spread uniformly on the hair, and the hair was shampooed with the same standard shampoo as in Example 1, and as a result, a soft and smooth feeling of hair was obtained without friction from bubbling to rinsing.

Example 9 and Comparative Example 5

The standard shampoo and hair rinse were produced, used to wash hair and evaluated in the same manner as in Example 1. The hair rinse was produced by using the composition shown in Table 4. Evaluation of feel upon using the standard shampoo when <treatment with the standard shampoo⇒ treatment in the Examples or Comparative Examples⇒ drying> was repeated 7 or times is shown in Table 5.

TABLE 4

| | Example 9 | Comparative product 5 |
|---|---|---|
| Copolymer 8 | 1.00 | |
| Amine-modified polysiloxane (KF - 8002 manufactured by Shin-Etsu Silicone Co., Ltd.) | | 1.00 |
| Behenyl trimethyl ammonium chloride | 1.00 | 1.00 |
| Stearamide propyl dimethylamine | 0.50 | 0.50 |
| Sstearyl alcohol | 1.00 | 1.00 |
| Behenyl alcohol | 3.00 | 3.00 |
| Dimethyl polysiloxane (10,000,000 cs:500 cs = 30:70) | 1.50 | 1.50 |
| Benzyloxy ethanol | 0.50 | 0.50 |
| Dipropylene glycohol | 1.00 | 1.00 |
| Isopropyl palmitate | 1.00 | 1.00 |
| Malic acid | 0.40 | 0.40 |
| Lactic acid | Suitable amount | Suitable amount |
| Perfume.methylparaben | Suitable amount | Suitable amount |
| Purified water | Balance | Balance |
| pH | 3.50 | 3.50 |

TABLE 5

| | Example 9 | | Comparative example 5 | |
|---|---|---|---|---|
| | After treatment repeated 7 times | After treatment repeated 14 times | After treatment repeated 7 times | After treatment repeated 14 times |
| Softness upon bubbling | ○ | ◎ | ○ | Δ |
| Softness upon rinsing | ○ | ◎ | ○ | Δ |
| Absence of feeling of friction upon rinsing | ○ | ○ | X | X |

As shown above, the hair during shampooing was gradually endowed with a good feeling, and stickiness and poor passage of hair through fingers, owing to the shampoo or rinse remaining in excess, did not occur even after the repeated treatment in this Example.

Evaluation Method 1 g of the standard shampoo was applied onto 20 g of 25 cm tress, bubbled for 30 seconds and rinsed for 30 seconds. Thereafter, 1 g of the rinse of the invention or the comparative rinse was applied thereto and rinsed for 30 seconds. Thereafter, it was dried. This procedure was repeated 7 or 14 times. Organoleptic evaluation was conducted under the following standards by a panel of 5 persons, and judgment was made on the basis of the average of evaluation points Softness During Bubbling 4: Very soft ◎: 3.0 to 4.0 on average 3: Slightly soft ○: 2.0 to 3 on average 2: Soft Δ: 1.0 to 2 on average 1: Not so soft x: 0 to 1.0

0: Not soft

Softness During Rinsing

4: Very soft

3: Slightly soft

2: Soft

1: Not so soft

0: Not soft

Absence of Feeling of Friction During Rinsing
    4: Not frictional
    3: Hardly frictional
    2: Not generally frictional
    1: Slightly frictional
    0: Significantly frictional

The invention claimed is:

1. A hair cosmetic comprising the following components (A), (B) and (C):
   (A) organopolysiloxane having an amino-modified organopolysiloxane chain and a polyoxyalkylene chain,
   (B) a tertiary amine compound represented by formula (2):

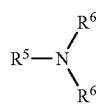

(2)

wherein $R^5$ represents a linear or branched alkyl or alkenyl group containing 8 to 35 carbon atoms in total, which may be interrupted by a functional group represented by —O—, —CONH—, —OCO— or —COO— or substituted with —OH; $R^6$ represents a C1 to C22 alkyl, alkenyl or hydroxyalkyl group, and two $R^6$s may be the same as, or different from, each other,
   (C) at least one compound selected from the group consisting of malic acid, succinic acid, maleic acid, salicylic acid, malonic acid, mandelic acid, lactic acid, glycolic acid and salts thereof,
   wherein the hair cosmetic has a pH of 3 to 5.

2. The hair cosmetic according to claim 1, wherein the amino-modified organopolysiloxane chain comprises a polymerization unit represented by formula (3):

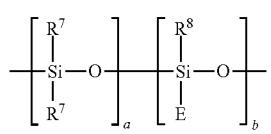

(3)

wherein $R^7$ represents a hydrogen atom or a C1 to C6 monovalent hydrocarbon group; $R^8$ represents $R^7$ or E, E represents a reactive functional group represented by —$R^9$—Z, wherein $R^9$ represents a direct bond or a C1 to C20 divalent hydrocarbon group and Z represents a primary to tertiary amino group-containing group or an ammonium group-containing group; a is a number of 2 or more; b is a number of 1 or more; and a plurality of $R^7$, $R^8$ and E may be the same as, or different from, one another.

3. The hair cosmetic according to claim 1, wherein component (A) is a block copolymer of an amino-modified organopolysiloxane chain and a polyoxyalkylene chain.

4. The hair cosmetic according to claim 1, wherein the component (A) comprises a polymerization unit represented by formula (4):

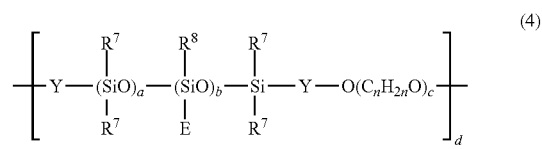

(4)

wherein $R^7$, $R^8$, E, a and b have the same meaning as defined above; n is a number of 2 to 10; $n_s$, whose number is c, may be the same as, or different from, one another; c is a number of 4 or more; d is a number of 2 or more; and Y represents a divalent organic group bound via a carbon-silicon atom to the adjacent silicon atom and via an oxygen atom to the polyoxyalkylene block chain.

5. The hair cosmetic according to claim 4, wherein the ratio of the siloxane block is 25 to 97% by weight of the whole block copolymer.

6. The hair cosmetic according to claim 1, which further comprises at least one lubricant selected from the group consisting of compounds represented by formulae (5), (6) and (7):

(5)

(6)

(7)

wherein $R^{10}$ represents a $C_{12}$ to $C_{30}$ alkyl or alkenyl group, $R^{11}$ represents a $C_{11}$ to $C_{29}$ alkyl or alkenyl group, at least one of $R^{12}$, $R^{13}$ and $R^{14}$ represents a $C_8$ to $C_{30}$ acyl group, and the remainder represents a hydrogen atom.

7. The hair cosmetic according to claim 2, wherein the component (A) is a block copolymer of an amino-modified organopolysiloxane chain and a polyoxyalkylene chain.

8. The hair cosmetic according to claim 2, wherein the component (A) comprises a polymerization unit represented by formula (4):

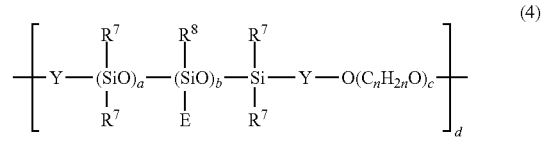

(4)

wherein $R^7$, $R^8$, E, a and b have the same meaning as defined above; n is a number of 2 to 10; $n_s$, whose number is c, may be the same as, or different from, one another; c is a number of 4 or more; d is a number of 2 or more; and Y represents a divalent organic group bound via a carbon-silicon atom to the adjacent silicon atom and via an oxygen atom to the polyoxyalkylene block chain.

9. The hair cosmetic according to claim 3, wherein the component (A) comprises a polymerization unit represented by formula (4):

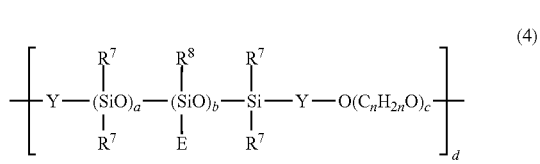

wherein $R^7$, $R^8$, E, a and b have the same meaning as defined above; n is a number of 2 to 10; $n_s$, whose number is c, may be the same as, or different from, one another; c is a number of 4 or more; d is a number of 2 or more; and Y represents a divalent organic group bound via a carbon-silicon atom to the adjacent silicon atom and via an oxygen atom to the polyoxyalkylene block chain.

10. The hair cosmetic according to claim 8, wherein the ratio of the siloxane block is 25 to 97% by weight of the whole block copolymer.

11. The hair cosmetic according to claim 9, wherein the ratio of the siloxane block is 25 to 97% by weight of the whole block copolymer.

12. The hair cosmetic according to claim 2, which further comprises at least one lubricant selected from the group consisting of compounds represented by formulae (5), (6) and (7):

wherein $R^{10}$ represents a $C_{12}$ to $C_{30}$ alkyl or alkenyl group, $R^{11}$ represents a $C_{11}$ to $C_{29}$ alkyl or alkenyl group, at least one of $R^{12}$, $R^{13}$ and $R^{14}$ represents a $C_8$ to $C_{30}$ acyl group, and the remainder represents a hydrogen atom.

13. The hair cosmetic according to claim 3, which further comprises at least one lubricant selected from the group consisting of compounds represented by formulae (5), (6) and (7):

wherein $R^{10}$ represents a $C_{12}$ to $C_{30}$ alkyl or alkenyl group, $R^{11}$ represents a $C_{11}$ to $C_{29}$ alkyl or alkenyl group, at least one of $R^{12}$, $R^{13}$ and $R^{14}$ represents a $C_8$ to $C_{30}$ acyl group, and the remainder represents a hydrogen atom.

14. The hair cosmetic according to claim 4, which further comprises at least one lubricant selected from the group consisting of compounds represented by formulae (5), (6) and (7):

wherein $R^{10}$ represents a $C_{12}$ to $C_{30}$ alkyl or alkenyl group, $R^{11}$ represents a $C_{11}$ to $C_{29}$ alkyl or alkenyl group, at least one of $R^{12}$, $R^{13}$ and $R^{14}$ represents a $C_8$ to $C_{30}$ acyl group, and the remainder represents a hydrogen atom.

15. The hair cosmetic according to claim 5, which further comprises at least one lubricant selected from the group consisting of compounds represented by formulae (5), (6) and (7):

wherein $R^{10}$ represents a $C_{12}$ to $C_{30}$ alkyl or alkenyl group, $R^{11}$ represents a $C_{11}$ to $C_{29}$ alkyl or alkenyl group, at least one of $R^{12}$, $R^{13}$ and $R^{14}$ represents a $C_8$ to $C_{30}$ acyl group, and the remainder represents a hydrogen atom.

16. The hair cosmetic according to claim 1, wherein the compound represented by formula (2) is at least one of behenyl dimethyl amine and stearamide propyl dimethylamine.

17. The hair cosmetic according to claim 13, wherein the lubricant is at least one of cetyl alcohol, stearyl alcohol and behenyl alcohol.

18. The hair cosmetic according to claim 1, wherein component (C) is malic acid or lactic acid.

19. A hair cosmetic comprising the following components (A), (B) and (C):
(A) 0.1 to 10% by weight of an organopolysiloxane having an amino-modified organopolysiloxane chain and a polyoxyalkylene chain,
(B) a tertiary amine compound represented by formula (2):

wherein $R^5$ represents a linear or branched alkyl or alkenyl group containing 8 to 35 carbon atoms in total, which may be interrupted by a functional group represented by —O—, —CONH—, —OCO— or —COO— or substituted with —OH; $R^6$ represents a C1 to C22 alkyl, alkenyl or hydroxyalkyl group, and two $R^6$s may be the same as, or different from, each other, (C) at least one compound selected from the group consisting of malic acid, succinic acid, maleic acid, salicylic acid, malonic acid, mandelic acid, lactic acid, glycolic acid and salts thereof, wherein the hair cosmetic has a pH of 3 to 5, wherein the component (A) is a block copolymer of an amino-modified organopolysiloxane chain and a polyoxyalkylene chain, and comprises a polymerization unit represented by formula (4):

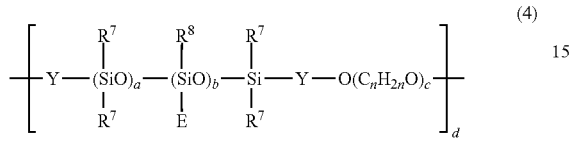

(4)

wherein $R^7$, $R^8$, E, a and b have the same meaning as defined above; n is a number of 2 to 10; $n_s$, whose number is c, may be the same as, or different from, one another; c is a number of 4 or more; d is a number of 2 or more; and Y represents a divalent organic group bound via a carbon-silicon atom to the adjacent silicon atom and via an oxygen atom to the polyoxyalkylene block chain.

20. The hair cosmetic according to claim 19, wherein the ratio of the siloxane block is 25 to 97% by weight of the whole block copolymer.

21. The hair cosmetic according to claim 19, which further comprises at least one lubricant selected from the group consisting of compounds represented by formulae (5), (6) and (7):

(5)

(6)

(7)

wherein $R^{10}$ represents a $C_{12}$ to $C_{30}$ alkyl or alkenyl group, $R^{11}$ represents a $C_1$ to $C_{29}$ alkyl or alkenyl group, at least one of $R^{12}$, $R^{13}$ and $R^{14}$ represents a $C_8$ to $C_{30}$ acyl group, and the remainder represents a hydrogen atom.

22. The hair cosmetic according to claim 19, wherein the compound represented by formula (2) is at least one of behenyl dimethyl amine and stearamide propyl dimethylamine.

23. The hair cosmetic according to claim 21, wherein the lubricant is at least one of cetyl alcohol, stearyl alcohol and behenyl alcohol.

24. The hair cosmetic according to claim 19, wherein component (C) is malic acid or lactic acid.

\* \* \* \* \*